(12) United States Patent
Chen

(10) Patent No.: US 10,167,446 B2
(45) Date of Patent: Jan. 1, 2019

(54) METHOD FOR INHIBITING CANCER CELLS AND TREATING DISEASES COMPRISING ADMINISTERING A FORMULA COMPOSITION OF ANTRODIA CINNAMOMEA

(71) Applicant: Cheng-Lin Agricultural Biotechnology Co., Ltd., Dounan Township (TW)

(72) Inventor: Min-Shih Chen, Dounan Township (TW)

(73) Assignee: CHENG-LIN AGRICULTURAL BIOTECHNOLOGY CO. LTD., Dounan Township (TW)

( * ) Notice: Subject to any disclaimer, the term of this patent is extended or adjusted under 35 U.S.C. 154(b) by 0 days.

(21) Appl. No.: 14/727,406

(22) Filed: Jun. 1, 2015

(65) Prior Publication Data

US 2016/0348063 A1    Dec. 1, 2016

(51) Int. Cl.
*C12N 1/14*    (2006.01)

(52) U.S. Cl.
CPC .................................... *C12N 1/14* (2013.01)

(58) Field of Classification Search
CPC . C12P 1/02; C12P 17/06; C12R 1/645; C12N 1/14; C12N 13/00; C12N 5/04; A61K 35/12; A61K 2300/00; A61K 36/07; A61K 31/136; A61K 31/138; A61K 31/404; A61K 31/513; A61K 31/575; A61K 2800/522; A61K 31/34; A61K 31/365; A61K 8/4913; A61K 8/4973; A61K 8/975; A61K 2236/19; A61K 31/09; A61K 31/122; A61K 35/074; A61K 36/076; A61K 36/185; A61K 36/28; A61K 36/481; A61K 45/06; A61K 36/06; A61K 2236/30; A61K 31/133; A61K 31/145; A61K 36/258; A61K 36/074; A61K 9/1652; A61K 9/4866; A61K 35/644; A61K 9/12; A61K 31/337; A61K 31/437; A61K 31/454; A61K 31/496; A61K 31/506; A61K 31/517; A61K 31/519; A61K 31/5377; A61K 31/69; A61K 31/715; A61K 39/0008; A61K 9/127; A61K 2039/55511; A61K 2039/55522; A61K 2039/55555; A61K 2039/55566; A61K 31/4985; A61K 31/7068; A61K 33/24; A61K 38/05; A61K 38/12; A61K 39/001; A61K 39/35; A61K 39/39; A61K 38/00; A61K 31/4015; A61K 36/00; A61K 39/0005; A61K 31/22; A61K 8/9706; A61K 31/555; A61K 38/44; A61K 8/99; A61K 31/341; Y10S 435/911; A01G 1/04; A01H 15/00; A01H 3/00; A01H 4/001; A01N 63/04; A01N 65/00; A01N 2300/00; A01K 51/00; A23K 10/30; A23K 20/10; A23K 20/111; A23K 20/163; A23K 50/90; A23K 20/00; A23K 20/147; A23K 20/158; A23L 33/145; A23L 2/52; A23L 33/105; A23V 2002/00; C07C 2601/16; C07C 403/02; C07C 403/08; C07C 403/10; C07C 403/20; C07C 49/753; C09D 5/008; C09D 5/1625; C09D 5/1668; C09D 7/1233; C09D 7/1291; D06M 16/003; C07H 15/10; G01N 2333/70557; G01N 2800/52; G01N 33/5011; G01N 33/57492; G01N 2333/4724; G01N 2333/485; G01N 2333/914; G01N 33/5008; G01N 33/57496; G01N 2500/10; B65D 75/002; B65D 75/36; A23F 5/02; C07K 14/375; C12Q 1/6886; C12Q 2600/106; C12Q 2600/118; C12Q 2600/158; Y02A 50/473; A61Q 19/02; A61Q 19/08; A61Q 19/00; A61P 35/00; A61N 5/10; C07J 71/0005; C07J 9/00; C07J 9/005
See application file for complete search history.

(56) References Cited

U.S. PATENT DOCUMENTS

| 6,355,475 | B1 * | 3/2002 | Huang | ...................... | C12N 1/14 435/254.1 |
|---|---|---|---|---|---|
| 6,391,615 | B1 * | 5/2002 | Huang | ...................... | C12N 1/14 435/171 |
| 6,395,271 | B1 * | 5/2002 | Huang | ...................... | C12N 1/14 424/115 |
| 8,524,486 | B2 * | 9/2013 | Tsai | ........................ | A01G 1/04 435/254.1 |

(Continued)

*Primary Examiner* — Deborah K Ware
(74) *Attorney, Agent, or Firm* — Muncy, Geissler, Olds & Lowe, P.C.

(57) ABSTRACT

A method for cultivating *antrodia cinnamomea* includes transplanting bacterial strains of *antrodia cinnamomea* into a petri dish receiving culture ingredients. The bacterial strains of *antrodia cinnamomea* are transferred into a culture container after mycelia of the bacterial strains of *antrodia cinnamomea* have grown to a predetermined area. The culture container receives a culture fluid. A formula composition of a culture medium for cultivating *antrodia cinnamomea* is added into the culture container after the mycelia of the bacterial strains of *antrodia cinnamomea* have grown in the culture container. The formula composition of the culture medium for cultivating *antrodia cinnamomea* includes growth basal ingredients and cultivating basal ingredients. The growth basal ingredients includes hydroxyhopanone. Mycelia of *antrodia cinnamomea* metabolize hydroxyhopanone precursors of agarwood during a growth procedure of the mycelia of *antrodia cinnamomea*, such that the mycelia of *antrodia cinnamomea* have a higher percentage of triterpenoids after fermentation.

1 Claim, 2 Drawing Sheets

(56) References Cited

U.S. PATENT DOCUMENTS

| | | | |
|---|---|---|---|
| 9,458,421 B2* | 10/2016 | Yang | C12N 1/14 |
| 2008/0102512 A1* | 5/2008 | Tsai | A01G 1/04 |
| | | | 435/256.8 |
| 2013/0028968 A1* | 1/2013 | Huang | 424/451 |

* cited by examiner

METHOD FOR INHIBITING CANCER CELLS AND TREATING DISEASES COMPRISING ADMINISTERING A FORMULA COMPOSITION OF ANTRODIA CINNAMOMEA

BACKGROUND OF THE INVENTION

The present invention relates to a method for cultivating *antrodia cinnamomea* and a formula composition of a culture medium for cultivating *antrodia cinnamomea* and, more particularly, to a method and a formula composition of a culture medium using a petri dish to cultivate *antrodia cinnamomea*.

Stout camphor tree is an endemic plant of Taiwan, is extremely valued, and is classified as one of protected plants. *Antrodia comphorata* only grows on stout camphor trees and is effective in inhibiting cancer, preventing transfer of cancer cells, and curing diseases including hepatitis B, diabetes, and high blood pressure. *Antrodia cinnamomea* is also effective in anti-oxidization and anti-blood clotting and in curing intestinal tract diseases. *Antrodia cinnamomea* has complicated ingredients. The main ingredients of *antrodia cinnamomea* include triterpenoids, superoxide dismutase (SOD), adenosine, and β-D-glucan. Triterpenoids are the most important ingredient and are the source of bitterness of the extract of *antrodia cinnamomea*. According to the current research results, the main effects of triterpenoids include improving immunity, inhibiting growth of cancer cells, inhibiting release of histamine, preventing allergy, improving liver functions, improving platelet aggregation, and reducing blood lipids. Thus, the more contents and species of triterpenoids, the more valuable in medical treatments. Experiments have proved that triterpenoids can effectively inhibit the activity of angiotensin converting enzyme (ACE) to thereby reduce the blood pressure. Triterpenoids can also provide an anti-inflammation effect.

However, *antrodia cinnamomea* is perennial, has a strong odor of a camphor tree, and has a shape of a plate or bell. Fresh *antrodia cinnamomea* has an orange-red surface which turns orange or yellow as it matures. *Antrodia cinnamomea* only parasitizes in caves of stout camphor tress which are endemic in Taiwan and grow in mountain areas having a height of 450-2000 m above sea level. After years of exploitation, stout camphor trees are rare and have been classified as a protected species under ecological protection. In the past, artificial culture of *antrodia* comphorata includes planting bacteria on diced sections of a stout camphor tree and growing the bacteria through environmental control. The ripe *antrodia* comphorata is taken out and processed into nutritive food. People in this industry must cultivate *antrodia* comphorata in mass production under the vast need in the market. Due to difficulties in obtaining the stout camphor tree sections and high costs, people in this industry developed a solid fermentation method and a liquid fermentation method. In the solid fermentation method, *antrodia* comphorata is contained in a packaging container to proceed with culture of mycelia. The packaging container receives a culture medium including fibers, carbohydrates, and cereals. Thus, *antrodia* comphorata can receive ingredients similar to wild *antrodia cinnamomea*. The culture takes about more than 3 months. Polysaccharide and triterpenoids change due to the ingredients of the culture medium. In the liquid fermentation method, liquid fermentation is carried out in a liquid fermentation container to obtain mycelia, requiring a small period of time for culture and having a lower cost. However, the nutritive ingredients of mycelia of *antrodia cinnamomea* are essentially polyose which can only generate a trace of triterpenoids.

Although the above methods for cultivating *antrodia comphorata* by fermentation can reduce the reliance on the stout camphor tree sections, triterpenoids only has a small percentage in the fermentation product of *antrodia* comphorata due to the formula composition for cultivating *antrodia* comphorata and the cultivating techniques. It is, thus, an important issue to solve the technical problems in developing the fermentation techniques for *antrodia cinnamomea*.

BRIEF SUMMARY OF THE INVENTION

According to an aspect, a formula composition of a culture medium is provided for cultivating *antrodia cinnamomea*. The formula composition of the culture medium includes growth basal ingredients and cultivating basal ingredients. The growth basal ingredients includes hydroxyhopanone. A percentage of the growth basal ingredients is less than 10% of the formula composition of the culture medium. Mycelia of *antrodia cinnamomea* fully use hydroxyhopanone precursors of agarwood during a growth procedure of the mycelia of *antrodia cinnamomea*, such that the mycelia of *antrodia cinnamomea* have a higher percentage of triterpenoids after fermentation.

The cultivating basal ingredients can be selected from the group consisting of brown rice, wheat, soybean, and combinations thereof.

The growth basal ingredients can be selected from the group consisting of powders, roots, stems, leaves, fruits, flowers of agarwood, and combinations thereof.

In another aspect, a method for cultivating *antrodia cinnamomea* includes a primary bacterial culture step, a transfer culture step, and a transforming culture step. The primary bacterial culture step includes transplanting bacterial strains of *antrodia cinnamomea* into a petri dish receiving culture ingredients. The transfer culture step includes transferring the bacterial strains of *antrodia cinnamomea* into a culture container after mycelia of the bacterial strains of *antrodia cinnamomea* have grown to a predetermined area. The culture container receives a culture fluid. The transforming culture step includes adding a formula composition of a culture medium for cultivating *antrodia cinnamomea* into the culture container after the mycelia of the bacterial strains of *antrodia cinnamomea* have grown in the culture container. The formula composition of the culture medium for cultivating *antrodia cinnamomea* includes growth basal ingredients and cultivating basal ingredients. The growth basal ingredients includes hydroxyhopanone. Mycelia of *antrodia cinnamomea* fully use hydroxyhopanone precursors of agarwood during a growth procedure of the mycelia of *antrodia cinnamomea*, such that the mycelia of *antrodia cinnamomea* have a higher percentage of triterpenoids after fermentation.

In an example, the culture ingredients are selected from the group consisting of yeast extract, glucose, konnyaku powders, honey, potato extract, and combinations thereof.

The culture ingredients can be a nutritional preparation providing propagation of *antrodia* comphorata and increasing adherence and growth of the bacterial strains of *antrodia cinnamomea*.

The culture fluid includes ingredients that can be selected from the group consisting of agarwood powders, yeast extract, glucose, honey, potato extract, and combinations thereof.

The cultivating basal ingredients can be selected from the group consisting of brown rice, wheat, soybean, and combinations thereof.

The growth basal ingredients can be selected from the group consisting of powders, roots, stems, leaves, fruits, flowers of agarwood, and combinations thereof.

The present invention will become clearer in light of the following detailed description of illustrative embodiments of this invention described in connection with the drawings.

DETAILED DESCRIPTION OF THE INVENTION

Figure 1:
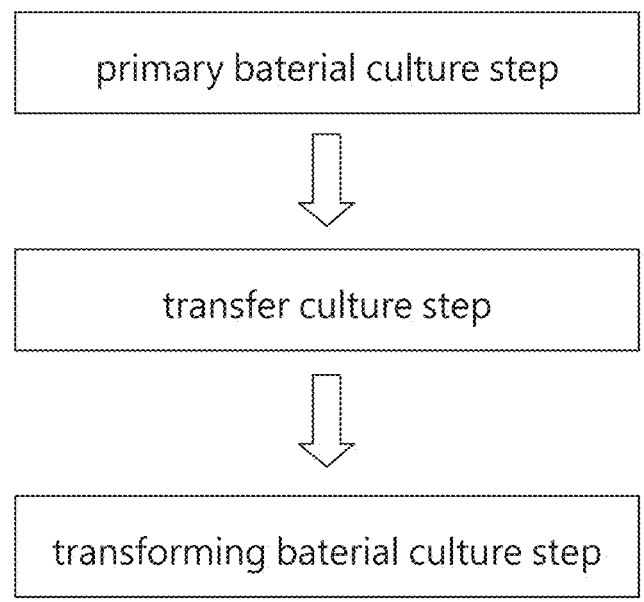
FIG. 1 is a flowchart illustrating a method for cultivating *antrodia cinnamomea* according to the present invention.

With reference to FIG. 1, a method for cultivating *antrodia cinnamomea* according to the present invention uses a formula composition of a culture medium for cultivating *antrodia cinnamomea* fermented by agarwood to increase the content of triterpenoids. Particularly, mycelia of *antrodia cinnamomea* can have more triterpenoids by using a special culture medium.

The method includes a primary bacterial culture step including transplanting bacterial strains of *antrodia cinnamomea* into a petri dish receiving culture ingredients before a culture process. The culture ingredients are selected from the group consisting of yeast extract, glucose, konnyaku powders, honey, potato extract, and combinations thereof. The yeast extract, glucose, honey, and potato extract are a nutritional preparation providing propagation of *antrodia comphorata*. The konnyaku powders provide aggregation to increase adherence and growth of the bacterial strains of *antrodia cinnamomea*.

In an example, the petri dish receives 5-15 wt % of yeast extract, 15-30 wt % of glucose, 1.5-2.5 wt % of konnyaku powders, 3-5 wt % of honey, and 10-15 wt % of potato extract.

The method further includes a transfer culture step. After the mycelia of the bacterial strains of *antrodia cinnamomea* have grown to 70%-80% of an area of the petri dish, the bacterial strains of *antrodia cinnamomea* are transferred into a culture container (such as an Erlenmeyer flask) that can be sealed. The culture container receives a culture fluid including ingredients selected from the group consisting of agarwood powders, yeast extract, glucose, honey, potato extract, and combinations thereof. The culture fluid contains carbon source, nitrogen source, and various trace elements required by fungi, such that the mycelia of *antrodia cinnamomea* can grow better.

In an example, the culture fluid received in the culture container includes 1-5 wt % of agarwood powders, 5-15 wt % of yeast extract, 15-30 wt % of glucose, 3-5 wt % of honey, and 10-15 wt % of potato extract.

The method further includes a transforming culture step. After the mycelia of the bacterial strains of *antrodia cinnamomea* have grown plump in the culture container, a formula composition of a culture medium for cultivating *antrodia cinnamomea* is added into the culture container. The formula composition of the culture medium for cultivating *antrodia cinnamomea* includes growth basal ingredients and cultivating basal ingredients, which are the main features of the present invention. The cultivating basal ingredients are selected from the group consisting of brown rice, wheat, soybean, and combinations thereof, providing basic nutrition for growth of the bacterial strains of *antrodia cinnamomea*. The growth basal ingredients include agarwood powders because they contain hydroxyhopanone. The mycelia of *antrodia cinnamomea* fully use hydroxyhopanone precursors of agarwood during a growth procedure of the mycelia of *antrodia cinnamomea*, such that the mycelia of *antrodia cinnamomea* have a higher percentage of triterpenoids after fermentation. The economic benefit is higher. Furthermore, agarwood powders are rich of linalool such that *antrodia* comphorata emits a specific fragrance after this procedure. After collection and post processing into a nutrient food, the taste effect can be increased when a user is eating the nutrient food. It can be appreciated that the growth basal ingredients used in this step are not limited to agarwood powders. Specifically, the growth basal ingredients can be selected from the group consisting of powders, roots, stems, leaves, fruits, flowers of agarwood, and combinations thereof.

In an example, after the mycelia of the bacterial strains of *antrodia cinnamomea* have grown plump in the culture container, liquid bacterial strains of *antrodia cinnamomea* were transplanted into solid cultivating basal ingredients including 1-5 wt % of agarwood powders. The cultivating basal ingredients containing cereals included 70-80 wt % of brown rice, 10-20 wt % of wheat, and 10-20 wt % of soybean, which were used as the formula composition of the culture medium, and 1-10 wt % of agarwood powders was added. The percentage of adenosine generated by the bacterial strains of *antrodia cinnamomea* increased significantly during the growth procedure using the cultivating basal ingredients containing solid cereals. Furthermore, the mycelia of *antrodia cinnamomea* fully used hydroxyhopanone precursors of agarwood powders as the basic compounds for triterpenoids during the growth procedure of the mycelia of *antrodia cinnamomea*, such that the percentage of triterpenoids of *antrodia cinnamomea* was significantly increased after the growth procedure using the solid culture medium.

In this example, the formula composition of the solid culture medium include brown rice, wheat, and soybean as the basic ingredients, and the percentage of agarwood powders was less than 10% of the formula composition of the culture medium. The agarwood powders provided the materials related to the precursors for combination of triterpenoids of the bacterial strains of *antrodia cinnamomea*. The triterpenoids generated by metabolism of *antrodia cinnamomea* can be increased after transplanting the bacterial strains of *antrodia cinnamomea* to the formula composition of the solid culture medium. The amount of triterpenoids generated after 120-day culture by an ordinary formula composition of culture medium is 238 mg/100 g. The amount of triterpenoids generated after 120-day culture by the formula composition of the culture medium including agarwood was 328 mg/100 g. The amount of adenosine was also increased from 346 mg/100 g (by an ordinary formula composition of culture medium) to 928 mg/100 g (by the formula composition of the culture medium including agarwood).

The fermentation products according to the present invention include triterpenoids and adenosine. The fermentation contents can be used to against inflammation and improve the immunity.

The fermentation products can be in any form acceptable in food science, including, but not limited to, capsules, tablets, powered drugs, liquid drugs, and colloids.

The fermentation products according to the present invention can be of any type of carriers acceptable in pharmacy, including, but not limited to, solvents, emulsifiers, suspending agents, decomposers, binders, excipients, stabilizers, chelating agents, diluting agents, gelating agents, preservatives, lubricants, surfactants, and adjuvants.

Figure 2:
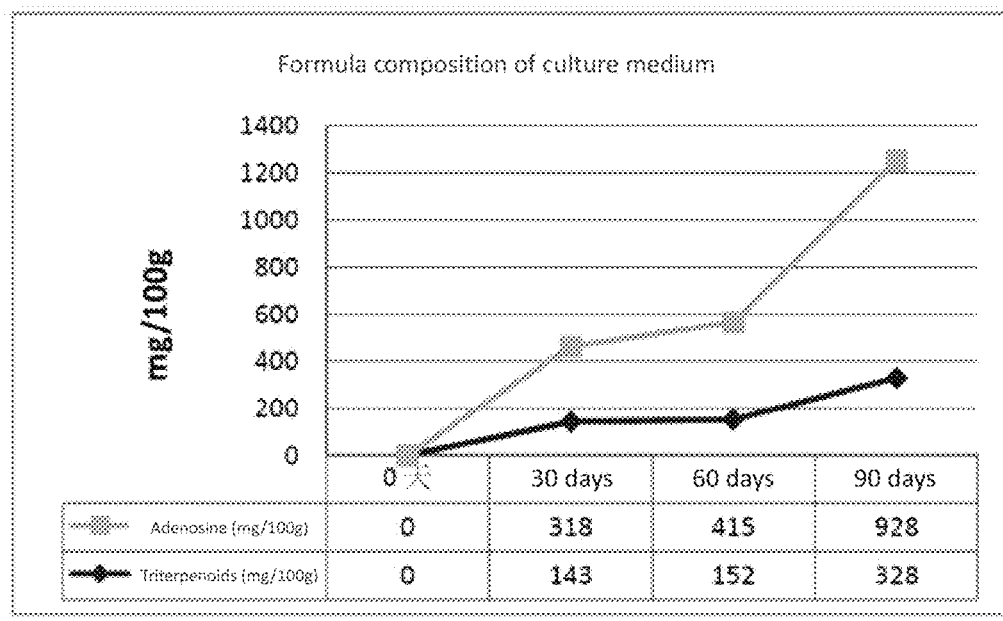
FIG. 2 is a diagram illustrating ingredients of a product obtained from agarwood powders through fermentation by bacterial strains of *antrodia cinnamomea*.

FIG. 2 is a diagram illustrating ingredients of a product obtained from agarwood powders through fermentation by bacterial strains of *antrodia cinnamomea* of an example of the present invention. The content analysis of acid EA soluble triterpenoids was conducted as follows. 3 g (fine weighing) of a sample was placed in a 250 mL conical flask. 100 mL 50% alcohol was added. The solution was oscillated at 100 rpm at room temperature. After 8-hour extraction, the clean solution was collected by using a centrifuge. The residuals were added with 100 mL 100% alcohol and then oscillated at 100 rpm at room temperature. After 12-hour extraction, the clean solution was added to proceed with filtration by a filter paper. Next, 30 mL 100% alcohol was used to wash the residuals on the filter paper. The filtration liquid was concentrated under a reduced pressure at 50° C. to an almost dry state. Next, 100 mL saturated $NaHCO_3$ solution was used to elute the concentrate in three batches. Then, 100 mL ethyl acetate (EA) was added to extract once. After removal of the ethyl acetate layer, 6N HCL was used to adjust the pH of the $NaHCO_2$ layer to a range between 3 and 4. Then, 100 mL ethyl acetate was added to extract three times. The ethyl acetate layer was collected and concentrated under a reduced pressure at 50° C. The concentrate solution was poured into a pre-weighed aluminum foil box and dried to a constant weight.

The content (percentage) of triterpenoids is equal to the weight of triterpenoids/sample weight*100%. The extract method for extracting adenosine from the fermentation products in *antrodia cinnamomea* was as follows. Sample powders were weighed in a 250 mL conical flask by fine weighing, and 100 mL RO water was added. The solution was oscillated by a supersonic device (Bransonic 5510) to proceed with extraction for 60 minutes and then separated by a centrifuge at 15,000 for 10 minutes. The upper, clean liquid was placed in a concentration bottle and concentrated under a reduced pressure at 50° C. to a certain amount. Then, deionized water was added until the total volume reached 10 mL. A 0.45 μm filter film was used to filtrate the solution. Then, analysis was carried out by using a high performance liquid chromatography. Adenosine standards having different concentrations were used as the standard curves for calibration.

The high performance liquid chromatography includes a Shimadzu LC10 AT VP pump and a Shimadzu UV-VIS detector and is connected to SISC 32 (Chinese version 2.1) made by Scientific Information Service Corporation (2634 Albany Ave. Davis Calif. 95616 U.S.A.) to process the data.

The conditions of high performance liquid phase chromatography were as follows:
(a) column: LiChrospher 100 RP-18 (250×4.6 mm, 5 μm, Merck).
(b) injection amount: 20 μL.
(c) detection wavelength: 260 nm.
(d) mobile phase: methyl alcohol : 0.02 M potassium dihydrogen phosphate=15:85

As can be seen from the above steps, the technical features of the present invention are that by using the special culturing steps and the culture medium, the low effective contents of triterpenoids in *antrodia cinnamomea* obtained by conventional methods can effectively be increased. According to the analysis result of the *antrodia cinnamomea* products by solid fermentation according to the present invention, the amounts of triterpenoids and adenosine were 143-328 mg/100 g and 318-928 mg/100 g, respectively. A product having a higher percentage of nutrients is obtained without using a large amount of camphor tree sections, providing a synergistic effect of enhancing environmental protection and improving human health.

Although specific embodiments have been illustrated and described, numerous modifications and variations are still possible without departing from the scope of the invention. The scope of the invention is limited by the accompanying claims.

What is claimed is:

1. A method for inhibiting cancer cells and treating hepatitis B, diabetes, high blood pressure and intestinal tract diseases by administering a formula composition of a culture medium for cultivating *Antrodia cinnamomea* to a patient in need thereof wherein the formula composition comprises:
   growth basal ingredients including hydroxyhopanone and agarwood powders, wherein the growth basal ingredients are further selected from the group consisting of roots, stems, leaves, fruits, flowers of agarwood, and combinations thereof; and
   cultivating basal ingredients, with a percentage of the growth basal ingredients being less than 10% of the formula composition of the culture medium, and with mycelia of *Antrodia cinnamomea* metabolizing hydroxyhopanone precursors of the agarwood powders during a growth procedure of the mycelia of *Antrodia cinnamomea*, such that the mycelia of *Antrodia cinnamomea* have an increased percentage of triterpenoids after fermentation,
   wherein the cultivating basal ingredients are selected from the group consisting of wheat, soybean, and combinations thereof.

* * * * *